(12) United States Patent
Halpern

(10) Patent No.: US 7,537,008 B2
(45) Date of Patent: May 26, 2009

(54) MANUAL VENTILATION OR RESUSCITATION DEVICE

(75) Inventor: Ian Loren Halpern, Palo Alto, CA (US)

(73) Assignee: ArtiVent Medical Corporation, San Francisco, CA (US)

(*) Notice: Subject to any disclaimer, the term of this patent is extended or adjusted under 35 U.S.C. 154(b) by 754 days.

(21) Appl. No.: 11/147,070

(22) Filed: Jun. 6, 2005

(65) Prior Publication Data

US 2006/0272644 A1 Dec. 7, 2006

(51) Int. Cl.
*A61M 16/00* (2006.01)
(52) U.S. Cl. ............................. 128/202.28; 128/205.13; 128/203.28
(58) Field of Classification Search ............ 128/200.24, 128/202.28–203.14, 203.22, 204.18, 204.28, 128/205.13–205.17, 898, DIG. 20, 203.28; 601/44, 148–152; 5/702, 710, 713; 297/284.6
See application file for complete search history.

(56) References Cited

U.S. PATENT DOCUMENTS

| | | | |
|---|---|---|---|
| 513,924 A | 1/1894 | Hartnett | |
| 527,248 A | 10/1894 | North | |
| 1,197,232 A | 9/1916 | Pierpont | |
| 1,202,125 A | 10/1916 | Tullar | |
| 2,217,575 A | 10/1940 | Hoff | |
| 2,300,273 A | 10/1942 | Connell | 128/203 |
| 2,711,170 A | 6/1955 | Bornstein | 128/203 |
| 2,902,992 A | 9/1959 | Reenvall | 128/29 |
| 2,999,495 A * | 9/1961 | Shipley | 600/541 |
| 3,046,978 A | 7/1962 | Lea | 128/29 |
| 3,461,866 A | 2/1966 | Ritchie | |
| 3,473,529 A | 10/1969 | Wallace | 128/145.7 |
| 3,818,806 A | 6/1974 | Fumagalli | 92/13.2 |
| 3,890,967 A * | 6/1975 | Elam et al. | 128/205.17 |
| 3,918,317 A * | 11/1975 | Claussen | 74/469 |
| RE29,317 E * | 7/1977 | Mosley et al. | 73/866.4 |

(Continued)

FOREIGN PATENT DOCUMENTS

WO WO/2006/120404 11/2006

OTHER PUBLICATIONS

U.S. Appl. No. 11/635,381, filed Dec. 6, 2006, Halpern et al.

(Continued)

*Primary Examiner*—Justine R Yu
*Assistant Examiner*—Annette F Dixon
(74) *Attorney, Agent, or Firm*—Knobbe, Martens, Olson & Bear LLP

(57) ABSTRACT

A manual ventilation or resuscitation device is provided. The body of the device has rigid panels that encompass a sealed volume and are movable with respect to each other. The body has a displacement in a direction of a hand displacement and at least one other direction. A size adjuster adjusts the body displacement(s) between the states. A frequency adjuster adjusts the time to restore the volume or to adjust the time to compress the volume. The body provides an ergonomic fit to a user's hand, which reduces fatigue. The volume and/or frequency adjustments provide a user with reliance on a more or less constant tidal volume and tidal rate. Such adjustments allow usage of the device on any patient, regardless of individual factors such as physical condition, body/lung size, age and sex. Multiple devices could easily be stacked or nested with each other, which reduces storage space.

22 Claims, 14 Drawing Sheets

U.S. PATENT DOCUMENTS

| | | | |
|---|---|---|---|
| 4,187,845 A | 2/1980 | Dror | 128/205.13 |
| 4,297,999 A | 11/1981 | Kitrell | 128/205.16 |
| 4,303,893 A * | 12/1981 | Goldberg | 331/1 A |
| 4,349,015 A * | 9/1982 | Alferness | 601/41 |
| 4,532,923 A | 8/1985 | Flynn | 128/205.13 |
| 4,591,271 A | 5/1986 | Byers | |
| 4,898,166 A * | 2/1990 | Rose et al. | 128/205.13 |
| 4,898,167 A * | 2/1990 | Pierce et al. | 128/205.16 |
| 4,934,360 A * | 6/1990 | Heilbron et al. | 128/205.16 |
| 5,305,739 A | 4/1994 | Gray | |
| 5,313,938 A | 5/1994 | Garfield et al. | |
| 5,345,929 A * | 9/1994 | Jansson et al. | 128/205.13 |
| 5,645,056 A | 7/1997 | Pomeroy | 128/205.13 |
| 5,704,348 A * | 1/1998 | Drews | 128/205.24 |
| 5,711,295 A * | 1/1998 | Harris, II | 128/202.28 |
| 5,787,880 A * | 8/1998 | Swanson et al. | 128/202.28 |
| 6,067,984 A | 5/2000 | Piper | |
| 6,493,200 B1 | 12/2002 | Farmer et al. | |
| 6,792,947 B1 | 9/2004 | Bowden | 128/205.17 |
| 7,392,805 B2 * | 7/2008 | Maguire | 128/205.14 |
| 2004/0173213 A1 | 9/2004 | Maguire | |
| 2005/0056277 A1 | 3/2005 | Lurie et al. | |
| 2005/0066976 A1 | 3/2005 | Wondka | |
| 2007/0169780 A1 * | 7/2007 | Halpern et al. | 128/205.15 |

OTHER PUBLICATIONS

International Search Report for PCT/US06/22011 (claiming priority to U.S. Appl. No. 11/147,070).

International Search Report for PCT/US07/86681 mailed Sep. 25, 2008.

* cited by examiner

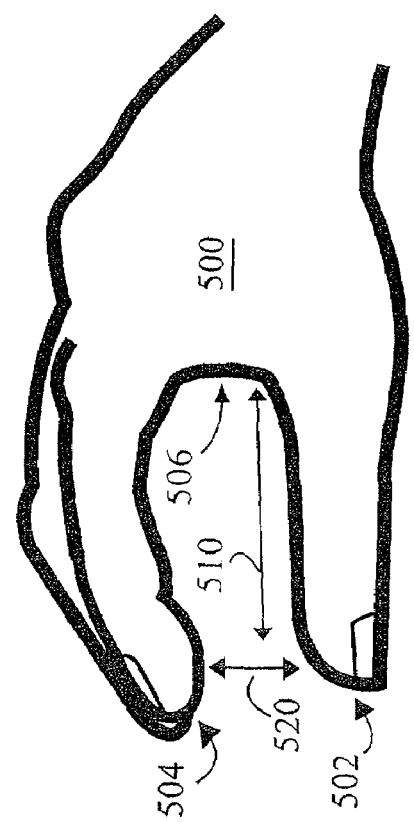
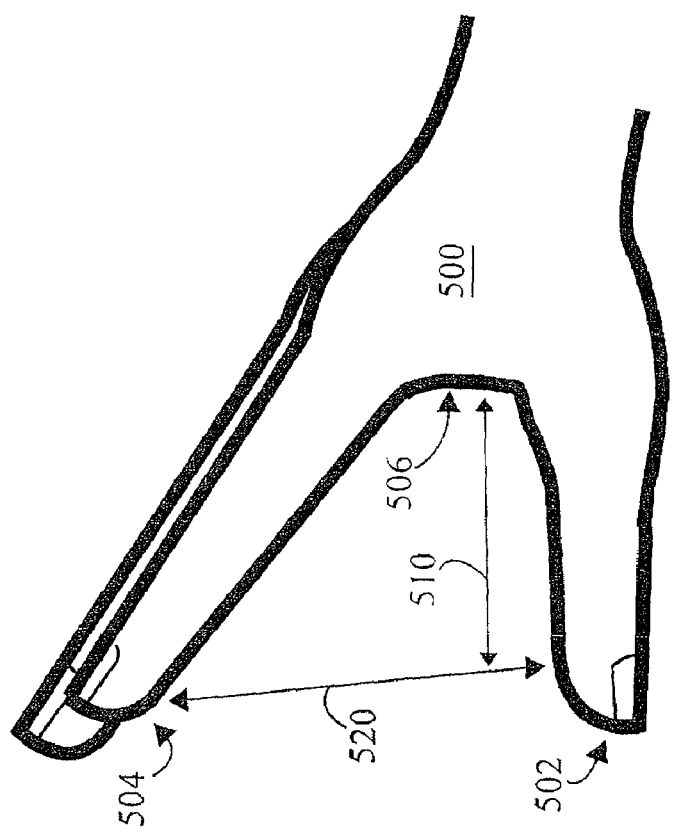
Fig. 5B
Fig. 5A

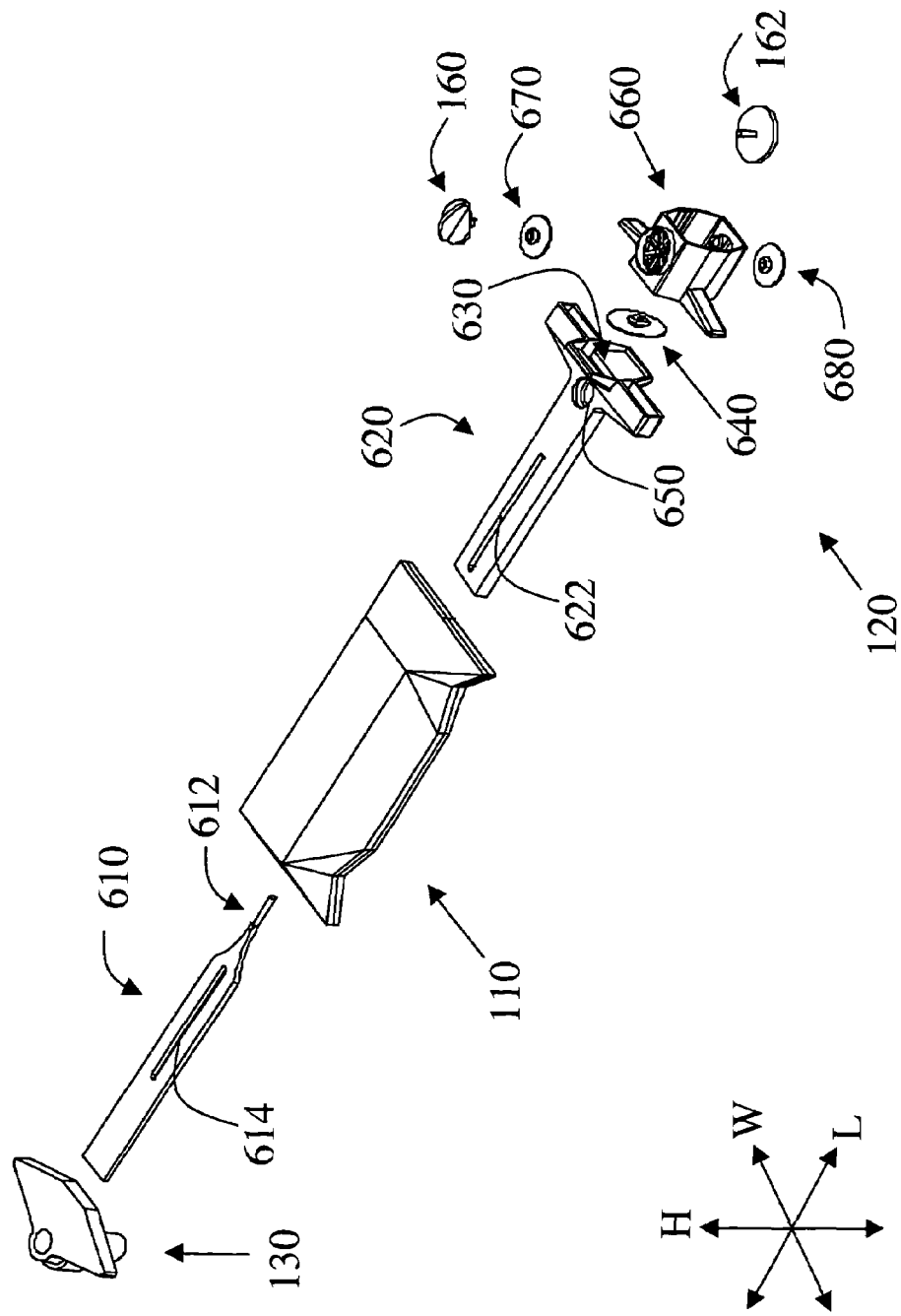
Figure 6 Exploded View

MANUAL VENTILATION OR RESUSCITATION DEVICE

FIELD OF THE INVENTION

The present invention relates generally to manual ventilation or resuscitation devices. More particularly, the invention relates to manual ventilation or resuscitation devices with control over the amount and rate of e.g. air, oxygen or oxygen-enriched air delivered to an individual and with a design that easily fits a user's hand.

BACKGROUND

Manual ventilation or resuscitation is performed on an individual when they are unable to breathe independently. Typically, this occurs when an individual is transported from one section of a hospital to another section such as an emergency room and an intensive care unit. Manual resuscitation also occurs during cardiopulmonary resuscitation (CPR), which is a standard technique applied to victims of cardiopulmonary arrest with the goal to re-establish normal cardiac and respiratory function.

Ventilation from a manual resuscitation device is currently provided by a self-filling elastomeric enclosure or bag. This bag is compressible by hand, a face-fitting mask (or intubation tube) in fluid communication with an outlet passage of the bag, and a one-way valve between the mask and bag to permit only fluid passage from the bag to the mask. The bag also has an inlet passage, typically with one opening for air and another, usually smaller opening for receiving oxygen. By squeezing the bag with their hand(s), a clinician delivers air or oxygen to an individual, then releases the bag to permit it to expand to full size and thereby draw air or oxygen through the inlet passage.

The amount of air received by the lungs of the individual corresponds to the volume of the bag. A larger bag provides a greater maximum volume of air to be pumped into the individual. Children and infants typically have smaller lungs than an adult, and therefore conventional manual resuscitation devices are provided in different sizes; e.g. infant, child and adult. Each size provides a different maximum volumetric output of air. Depending on factors such as physical condition, body size, age, sex, etc., each individual may require a specific volume of air, i.e. tidal volume, and frequency, i.e. tidal volume/minute.

Unfortunately, current manual ventilation or resuscitation devices are not suitable for the desired monitoring and control of tidal volume delivery. For instance, the collapsible bag portion of the resuscitation device allows the user to merely "feel" the amount of air they are providing to the individual. This provides them a rough estimate of the volume of air they are providing and a tactile feel for when the lungs are non-compliant, i.e. are being pressurized. Although self-filling respiration (resuscitation) enclosures or bags can be selected on the basis of known maximum volumes, the volume actually delivered can vary substantially among several operators, dependent upon factors such as hand size, number of hands used, technique, enthusiasm and fatigue. These variations have been shown to be as much as 60 percent of the optimal tidal volume. Frequency can also vary between users.

Accordingly, it is considered an advance in the art to develop a single manual ventilation or resuscitation device that can be used on any patient, regardless of individual factors such as physical condition, body/lung size, age and sex.

SUMMARY OF THE INVENTION

The present invention is a single manual ventilation or resuscitation device. The body of the device has rigid panels that encompass a sealed volume with an inlet mechanism and an outlet mechanism. The rigid panels are movable with respect to each other to allow the body to move between an uncompressed state and a compressed state. Once in compressed state a volume restoring mechanism is responsible to restore the volume from the compressed state back to the uncompressed state.

One of the key objectives of the invention is to be able to hold the body with one hand and to compress the body with that one hand. To meet this objective, in one embodiment, the body is characterized by having a displacement in a direction of a hand displacement (e.g. height of the body) and at least one other direction (e.g. width of the body) other than this hand displacement. In another embodiment, the body is characterized by having a displacement in a direction of a hand displacement (e.g. height of the body) and at least two other directions (e.g. width and length of the body) other than this hand displacement. The displacement in width and/or length is a function of the height displacement and the geometry of the rigid panels.

The displacement of a panel are up to 85 mm, preferably up to 20-25 mm, and more preferably 10-15 mm. Some of the displacements would have to comfortably fit between the thumb, one or more fingers and the web of the hand. In other words, the natural range of a grasping motion of a hand defines these displacements. The volume changes between the states ranges from 1 to 500 cc (infant and child), 250 to 1200 cc (child to adult), or 1 to 1400 cc (infant to adult).

A size adjuster is included to adjust one or more of the body displacements to change the dimension of the uncompressed state or volume. These size adjustments are up to 170 mm, and preferably up to 25 mm. The objective of the size adjuster is to adjust the displacement to then adjust the volume of e.g. the air delivered to an individual. Hence the size adjuster is also referred to as a volume adjuster.

A frequency adjuster is included to adjust the time to restore the volume from the compressed state to the uncompressed state or to adjust the time to compress the volume from the uncompressed state to the compressed state.

Feedback mechanisms could be included to provide tactile feedback, visual and/or audible feedback to the user. An example of tactile feedback is to include tactile feedback areas, e.g. a flexible material, to cover an opening in a rigid panel. These areas allow the user to feel the compression force or lung resistance. These tactile areas are preferably sized and positioned to fit a thumb or one or more fingers of the user's hand. An example of a visual feedback mechanism is to provide the user feedback over the size (volume) adjustments or the frequency. An example of an audible feedback mechanism is to provide the user feedback over e.g. the compression speed, frequency, tidal volume, setting of the size (volume) adjuster or setting of the frequency control adjuster.

One advantage of the device is the ergonomic fit of the body to a user's hand in both uncompressed and compressed state, which reduces fatigue to hand and/or arm muscles. Another advantage of the device is the ability to adjust the volume and/or frequency so that the user can rely on a more or less constant tidal volume and tidal rate. Such ability allows one to use the device on any patient, regardless of individual factors such as physical condition, body/lung size, age and sex. Yet another advantage is that multiple devices could easily be stacked or nested with each other. In exemplary embodiments, the design and geometry could be configured to include such stacking or nesting capabilities.

BRIEF DESCRIPTION OF THE DRAWINGS

The objectives and advantages of the present invention will be understood by reading the following detailed description in conjunction with the drawings, in which:

FIGS. 5A-5B show a hand with dimension for grasping and operating the device, the device being in an uncompressed state (FIG. 5A) and a compressed state (FIG. 5B), according to one embodiment of the invention.

FIG. 6 shows an exploded view of the device according to the present invention.

DETAILED DESCRIPTION

Although the following detailed description contains many specifics for the purposes of illustration, anyone of ordinary skill in the art will readily appreciate that many variations and alterations to the following exemplary details are within the scope of the invention. Accordingly, the following preferred embodiments of the invention are set forth without any loss of generality to, and without imposing limitations upon, the claimed invention.

Figure 1:
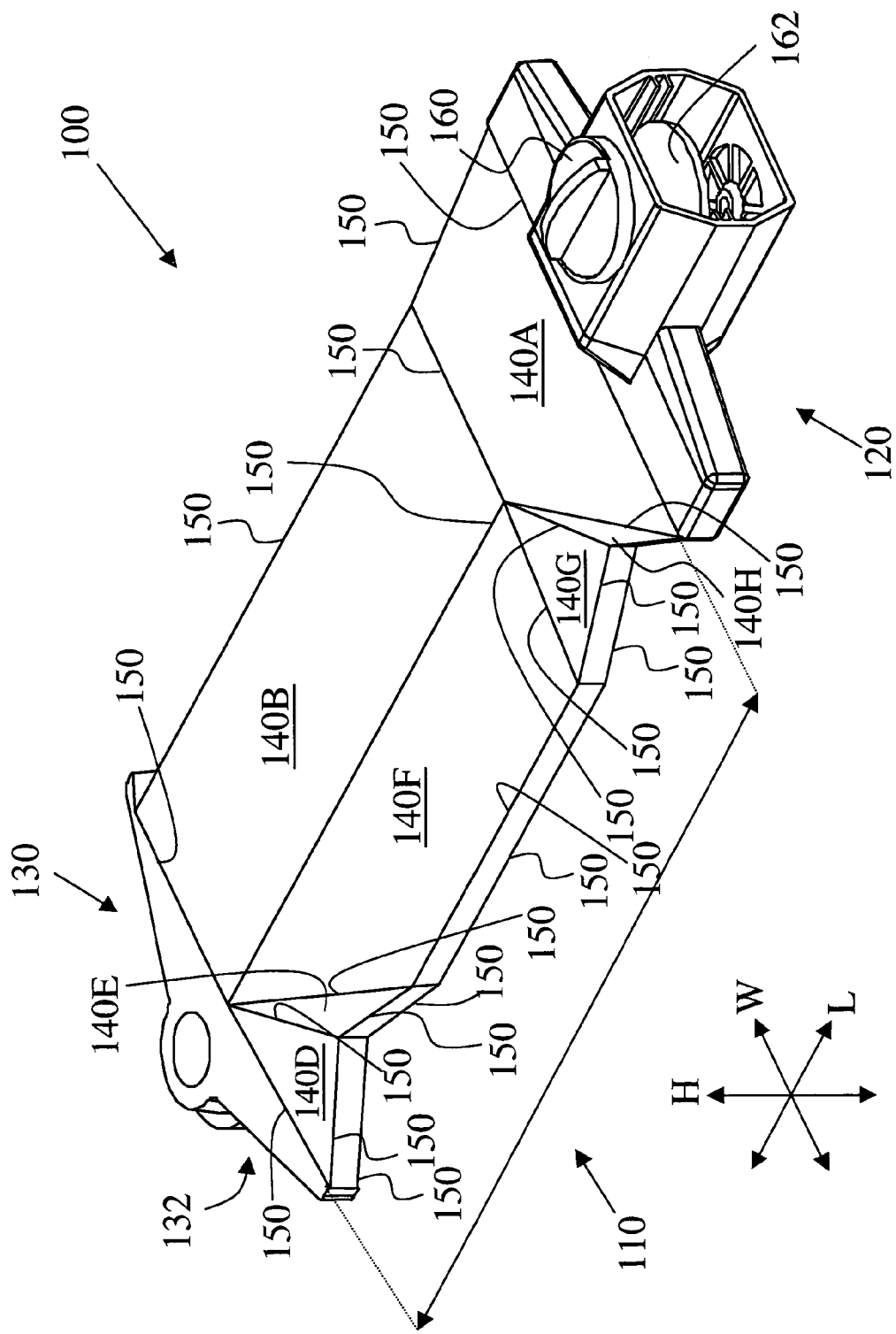
FIG. 1 shows a three-dimensional perspective of the device according to the present invention.

A three-dimensional view of one example of the ventilation or resuscitation device 100 is shown in FIG. 1. In general, three parts can be distinguished: a body 110, an input mechanism 120 to allow input of e.g. air, oxygen, oxygen-enriched air, fluid, fluid mixture, gas, gas mixtures or any combination or derivative thereof in body 110, and an output mechanism 130 to output and deliver some or all of the inputted content from body 110 to an individual via connector 132. Body 110 distinguishes rigid panels that are movable with respect to each other. The key idea of the design of body 110 with rigid panels is to encompass a volume that can contain e.g. air, oxygen or oxygen-enriched air. Another key idea of the invention is to be able to hold the body of the device with one hand and to compress the body with that one hand. The concept as conceived in this invention, as will be clear from reading the description, could be generalized to a body with rigid panels whereby the body is characterized as having a displacement in a direction of a hand displacement and at least one other direction other than that particular hand displacement.

In the particular example of FIG. 1 body 110 distinguishes a plurality panels; e.g. panels forming the top, panels forming the bottom, and panels for each side. More particularly, the following (main) panels can be distinguished, i.e. panels 140A, 140B, 140D, 140E, 140F, 140G and 140H, which are all visible in FIG. 1; panels 140D, 140E, 140F, 140G, 140H, 140D', 140E', 140F', 140G', 140H', which are all visible in FIG. 2; panels 140A, 140B, 140C, 140D, 140E, 140F, 140G, 140H, 140D", 140E", 140F", 140G" and 140H", which are all visible in FIG. 3; and panels 140C and 140C', which are all visible in FIG. 4. Panels blocked from the views in FIGS. 1-4, are 140A', 140B', 140D''', 140E''', 140F''', 140G''', 140H'''. The relative positions and orientations of the panels blocked in the figures is readily appreciated by a person of average skill in the art to which this invention pertains.

Figure 2:
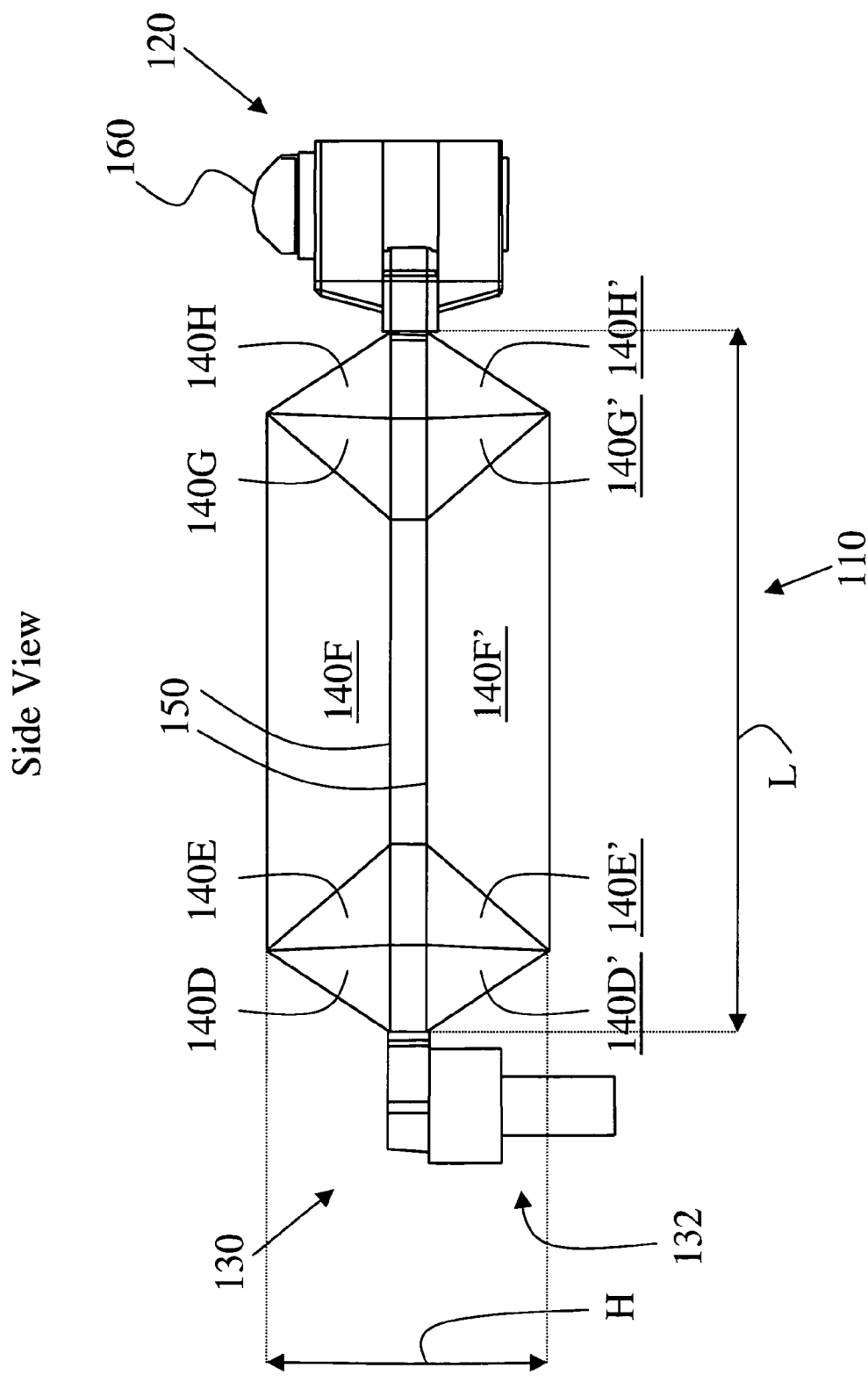
FIG. 2 shows a side view of the device according to the present invention.
Figure 3:
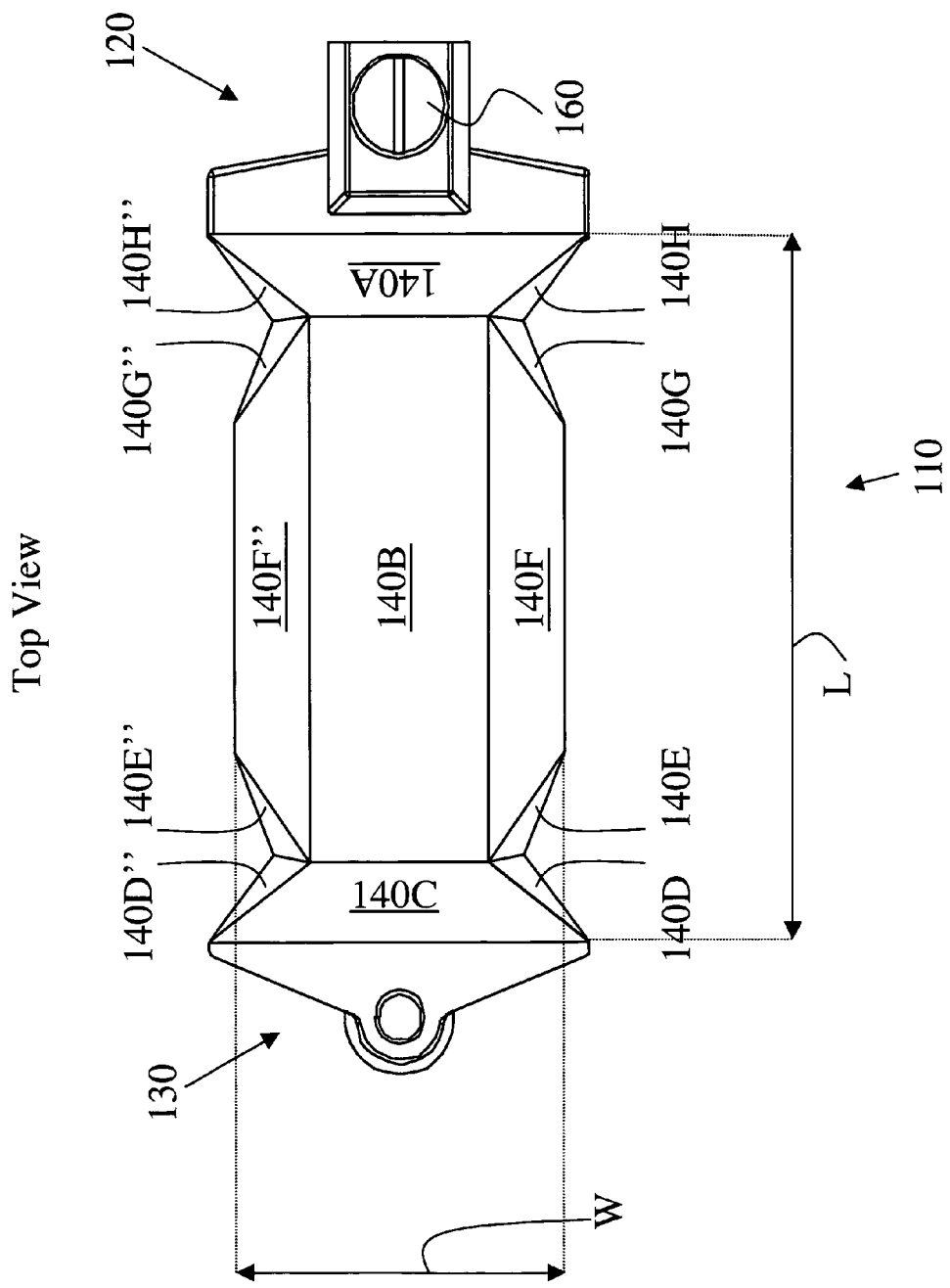
FIG. 3 shows a top view of the device according to the present invention.
Figure 4:
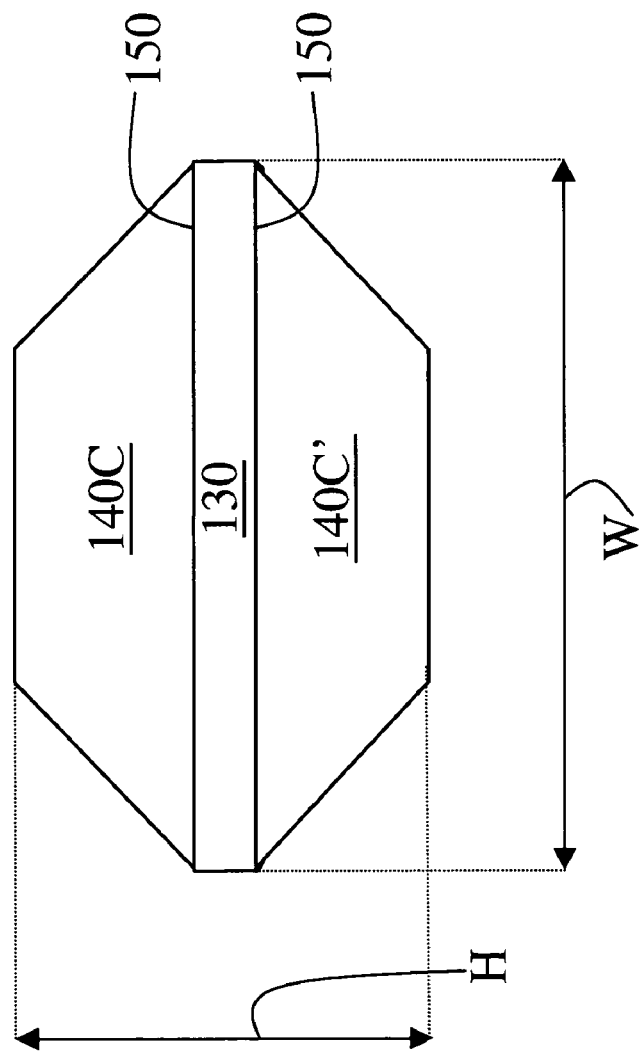
FIG. 4 shows a front view of the body of the device according to the present invention. The hook-up to a mask or intubation tube and outlet is left out for clarity.

The movable parts or structures, indicated by 150 in FIGS. 1, 2 and 4 could be living joints/hinges, snaps joints, fabricated flexures, heat-shrinked joints or flexures, welded joints, simple mechanical hinges, pinned hinges, flexible hinges, or the like. The type of movable structure depends on the type of manufacturing that is used to create the rigid panels and body. Examples of different types of manufacturing of the panels, movable structures and body are e.g. blow molding, heat sealing, overmolding, the mechanical assembly of a rigid paneled chassis with a flexible bladder or skin to form the body, coining to form living hinges, assembly using gaskets as seals in hinges, injection molding, ultrasonic welding, radio frequency welding, dielectric welding, high frequency welding, dipping, extrusion, spray coating, brush on, assembly of adhesive backed sheets of various materials, and/or any type of manufacturing that results in a body with rigid panels that are movable with respect to each other. A person of average skill in the art to which this invention pertains would readily appreciate the different types of manufacturing that can be used to make body 110, which are known techniques in the mechanical and design engineering art. Input mechanism 120 and output mechanism 130 could be manufactured and integrated along with the manufacturing process of body 110 or later assembled to body 110. The types of materials that can be used for the rigid panels, input mechanism 120, output mechanism 130 and other structures of the device are e.g. polymers, plastic, polyethylene, polycarbonate, high impact polystyrene, K-resin, ABS, PVC, acetal, polypropylene, silicone, thermoplastic elastomers, thermoplastic rubbers, latex, fabrics, cardboard, or the like.

Body 110 has an uncompressed state where the panels are positioned to create a volume that can be filled with e.g. air, oxygen or oxygen-enriched air. From the uncompressed state, body 110 can change to a compressed state where the panels are moved with respect to each other to decrease the volume with respect to the volume in the uncompressed state. In other words, moving the rigid panels with respect to each other from the uncompressed state to the compressed state, air, oxygen or oxygen-enriched air is outputted via output mechanism 130. The uncompressed state could be at full expansion (i.e. maximum volume) or any intermediate state (See also size adjuster (volume) description). Restoring the volume allows entry of new air, oxygen or oxygen-enriched air into the volume via input mechanism 120.

Figure 1A:
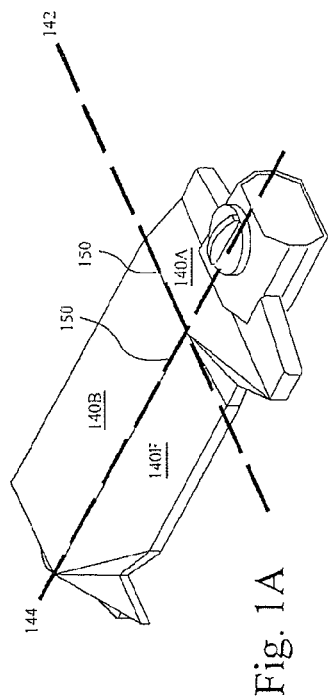
FIGS. 1A-1C are perspective views illustrating an embodiment of the device in an uncompressed (FIG. 1A), partially compressed (FIG. 1B), and fully compressed (FIG. 1C) state, according to one embodiment of the invention.
Figure 1B:
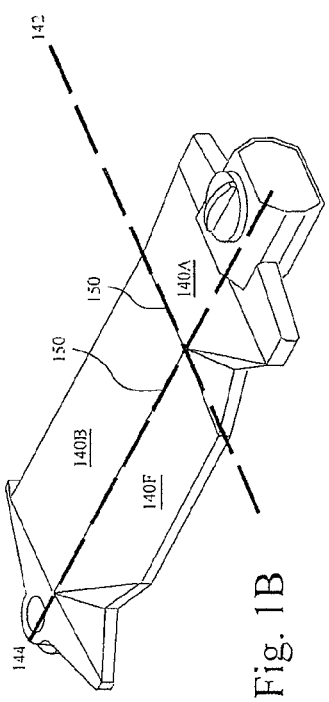
Figure 1C:
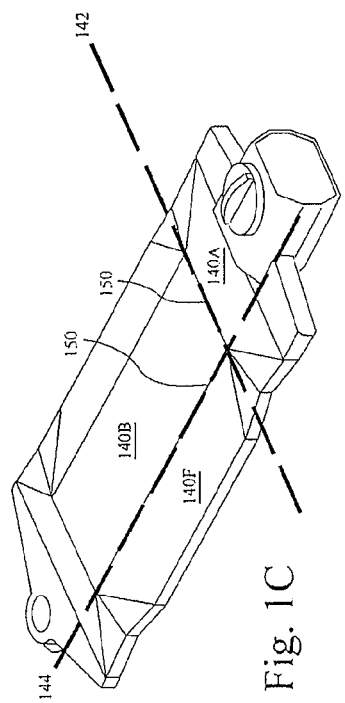

Body 110 has a height H, width W and length L (see FIGS. 1-4). In general, the state changes of body 110 could be characterized by the height H of body 110 being larger in the uncompressed state compared to the compressed state. FIGS. 1A-1C are perspective views illustrating an embodiment of the device in an uncompressed (FIG. 1A), partially compressed (FIG. 1B), and fully compressed (FIG. 1C) state. The height changes cause changes in width W and length L, which are smaller in the uncompressed state compared to the compressed state. The width and length changes are a function of the height changes and the geometry of panels as a person of average skill would readily appreciate. It is further noted that the body could be characterized by having at least two of the panels capable of rotating around substantially orthogonal axes with respect to each other; consider e.g. panels 140F and 140C which are both involved in the height changes, but given their orientation, 140F is further related to the width changes, and 140C is further related to the length changes. One illustrative example is shown in FIGS. 1A-1C, where panels 140B and 140F rotate around axis 144, which is substantially orthogonal to axis 142 which panel 140A rotates around. In summary, the body is characterized as having a displacement in a direction of a hand displacement (i.e. height of body) and at least two other directions (i.e. width and length of body) other than the particular hand displacement (i.e. height of body).

The body could also have a higher or a smaller number of panels than body 110, as a person of average skill in the art to which this invention pertains would appreciate. For example, the panels could be assembled radially around central top and bottom panels and more panels can be added, for example, 140F can be broken up into two or more panels. An example of reducing panel numbers could be achieved by reducing 140A, 140B and 140C to only two panels. In the latter example the body would have height and width or length changes. In summary, such bodies could be characterized as having a displacement in a direction of a hand displacement (i.e. height of body) and at least one other direction (i.e. width or length of body) other than the particular hand displacement (i.e. height of body).

As mentioned above, one of the key objectives of the invention is to be able to hold the device with one hand and to be able to compress the body with that one hand. To meet the objective the height and width changes in uncompressed and compressed state are therefore constrained since they would need to fit: (i) the hand of a user and (ii) the grasping (or squeezing) range of motion of the user.

Furthermore, the thumb and one or more fingers are desirably positioned on body 110 to create a mechanical advantage (i.e. a large moment arm with respect to the point of rotation) when compressing the body. Such a mechanical advantage meets another objective of the invention, which is to reduce fatigue of the hand muscles and potentially also the arm muscles.

Figure 5:
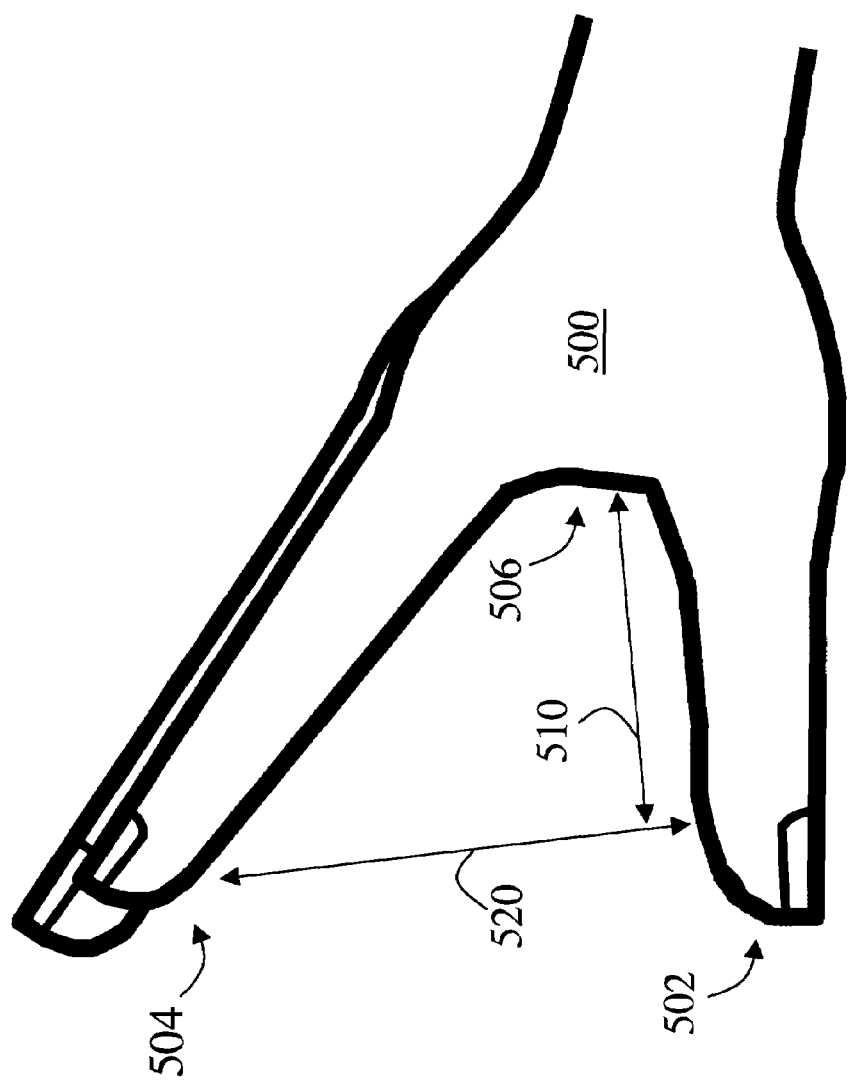
FIG. 5 shows a hand with dimensions for grasping and operating the device according to the present invention.

FIG. 5 shows hand 500 with thumb 502, one or more fingers 504 and web of the hand 506 between which body 110 is typically held. Given a variety of hand sizes (e.g. male, female, large and small) in mind one could determine a reasonable range of motion and a comfortable fit to the user's hand that constrains the height and width dimensions of body 110 when moving between the uncompressed state (e.g., the hand position illustrated in FIG. 5A) and a compressed state (e.g., the hand position illustrated in FIG. 5B). For example, the height and width (displacement) changes of a single panel could be up to 85 mm, preferably 20-25 mm and more preferably up to 10-15 mm. The height changes would correspond to a hand displacement 520 in FIG. 5 and the width changes would correspond to a hand displacement 510 in FIG. 5. A person of average skill in the art to which this invention pertains would readily appreciate that the geometry (dimensions and relative angles) of the panels could be varied to meet the desired height and width (displacement) changes as well as the desired deliverable tidal volume.

The length changes of a single panel could also be up to 85 mm but will not be constrained by hand dimensions, but will be a variable in determining the change in volume. The change in volume typically ranges from 1 to 1400 cc, preferably from 250 to 1200 cc, which covers tidal volume ranges for children and adults. When the device is used for infant or child purposes the volume changes are smaller and preferably range from 1 to 500 cc.

FIG. 6 shows an exploded view of an embodiment of the device of the invention. In addition to the elements discussed above the device further includes a main shaft 610 connected to output mechanism 130 and positioned inside body 110. Main shaft 610 has narrow (cylindrical) end 612 and a slot 614. The device further has a receiving shaft 620 connected (or could be a single part) to input mechanism 630 and also positioned inside body 110. Receiving shaft 620 has an opening (not visible in figure) sized to allow travel of main shaft 610 along the length of receiving shaft 620. It further has a slot 622 preferably of equal size as slot 614; slots 614 and 622 should also be aligned with each other as will be understood when discussing volume recovery from compressed state to uncompressed state with respect to FIG. 8. Opening 630 could be sized such that element 660 could be mechanically assembled by ultrasonic welding, snap fit, press fit, adhesive or any other known techniques in the mechanical and design engineering art. Element 660 allows fitting and attachment of air/oxygen input devices. A flutter valve 640 is fitted to the front opening of element 660 allowing e.g. air travel into receiving shaft 620 through opening 650 and then into body 110. Element 660 further houses a size adjuster (also referred to as volume adjuster).

In general, the size adjuster of the device adjusts the length changes, width changes and/or height changes. The size adjuster serves the purpose of easily adjusting the deliverable volume so that the user can rely of a fairly constant volume of deliverable e.g. air, oxygen or oxygen-enriched air. Adjusting the deliverable volume is important to compensate for factors such as physical condition, body size, age, sex, etc.

In a preferred embodiment, size adjuster is integrated with input mechanism 120, in particular with element 660, and adjusts the travel length of body 110. The size adjuster distinguishes an adjustment knob 160 placed on top of element 660 and conveniently accessible to a user. The adjustment knob 160 is connected to an adjustment dial 162, which in this example is positioned inside element 660; the connection could e.g. be through either valve 670 or 680.

Figure 7:
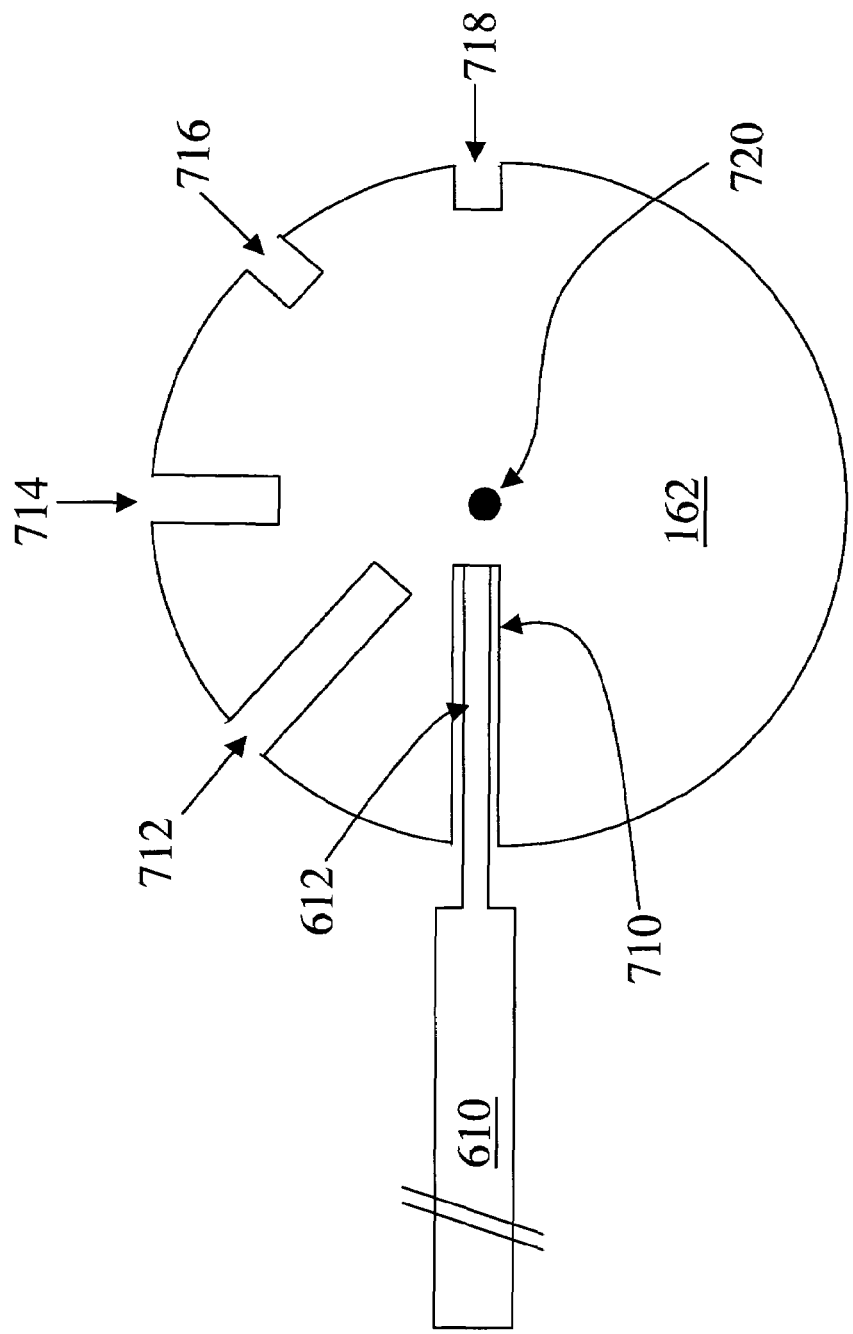
FIG. 7 shows an example of a size (volume) adjuster of the device according to the present invention.

FIG. 7 shows adjustment dial 162 with a number of slots 710, 712, 714, 716 and 718. These slots are sized to fit narrow (cylindrical) end 612 of main shaft 610 that is able to travel all the way through the opening of receiving shaft 620 (as well as through flutter valve 640; not shown in figure) when moving between uncompressed and compressed states. By changing adjustment knob 160, adjustment dial 162 is rotated around pivot 720 to a new slot position; this is typically done when the body is in compressed state. It is noted that size adjuster changes the dimension of the uncompressed state or volume.

Slots restrict the travel distance of main shaft 610 and therewith control the deliverable volume to an individual. Slots sizes could be up to 170 mm to allow changes in length, and preferably are up to 25 mm. The number of slots and the sizes of the slots are selected to cover a reasonable range of deliverable tidal volumes as a person skilled in pulmonary or emergency medicine would readily appreciate.

In the example of FIG. 7, the size (length) (volume) adjuster is placed outside body 110. A person of average skill in the art to which this invention pertains would appreciate that the size adjuster can also be positioned inside the body or intrinsic to the design of the body. Furthermore, the size adjuster could also be added for width or height control or any combination of height, length or width, or any other direction in a similar fashion as shown in FIG. 7.

Instead of a size adjuster with slots, one could design and integrate different types of mechanisms, which are all within the scope of the present invention. Examples of such variations are e.g. an adjustable threaded stop for the main shaft, an element with chambers whereby each chamber has grooves or each chamber has different depths, a slotted tube with different positions of the slots to set travel constraints to the main shaft, deflecting stops that deflect when adjusted in an incorrect or uncompressed state, a rack and pinion system with stops, ratcheting band (adjustable zip-tie), adjustable cam, a rotating dial of spring loaded stops that deflect when adjusted in an incorrect or uncompressed state, or any type of engineering mechanism that constrains the travel of the main shaft to control the volume output.

Figure 8:
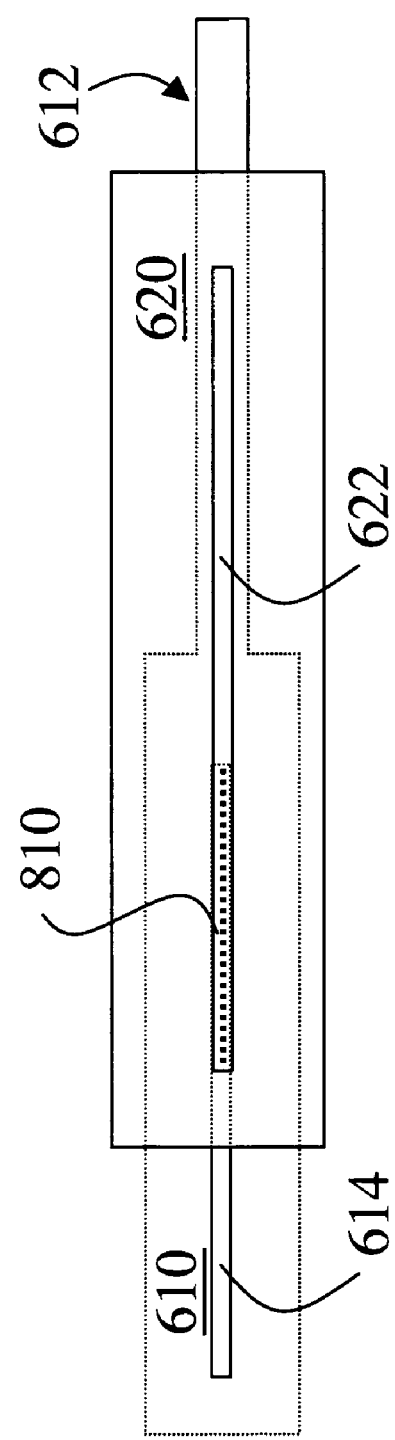
FIG. 8 shows an example of a mechanism to restore the volume of the body of the device from a compressed state to an uncompressed state according to the present invention.

FIG. 8 shows an example of a volume restoring mechanism to restore the volume from a compressed state back to the uncompressed state. This could be accomplished by main shaft 610 traveling inside receiving shaft 620 whereby (part of) slots 614 and 622 travel inline with each other. One site of slot 614 is connected to an opposite site of slot 622 by element 810, which is e.g. an extension spring, plastic or rubber. When we change from uncompressed state to compressed state, force is built-up in element 810. This force is then used to restore the body back to the uncompressed state when the user releases the compression force applied to body 110. As a person of average skill in the art to which this invention pertains would appreciate, the volume restoring mechanism could also be outside body 110 or intrinsic to body 110 (e.g. one could have the restoring force as an intrinsic property of the movable joints 150). Other alternatives are a leaf spring mechanism inside body 110 that builds up force when compressed or an extension spring/mechanism placed inside body 110 but not integrated with the two shafts. The volume restoring mechanism could be adjusted using similar techniques as discussed for the size (volume) adjuster or it could be left to one setting.

In an alternate embodiment, the device includes a frequency adjuster to set and control the time to: (i) restore the volume from a compressed state back to the uncompressed state, and/or (ii) compress the volume from uncompressed state to a compressed state. The volume restoring mechanism as discussed above could be used as a frequency adjuster/controller. However, in this scenario, the frequency control is then still in hand of the user and not constrained by the device. Control over frequency is desired to enforce consistency in tidal volume rate. Therefore in another embodiment a frequency adjuster is added in a similar fashion as the size adjuster.

A frequency control knob could be placed at the opposite site of element 660 and implemented to adjust the frequency by e.g. a rack and pinion mechanism in combination with the main shaft to set the dampening of travel of the main shaft, a rack and pinion mechanism coupled with rotationally resistant gears, a polymer escapement mechanism, a friction brake, a rotationally resistant ratchet wheel, or a track to deflect the travel of the main shaft. All such mechanisms, which are known in the mechanical and design engineering art, can be adjusted via a frequency control knob to change the dampening of the travel of the main shaft, whereby an increase in dampening would result in a decrease in frequency. Similarly to the size adjuster mechanism, the frequency adjuster could also be inside the body, outside the body or intrinsic to body.

Figure 9:
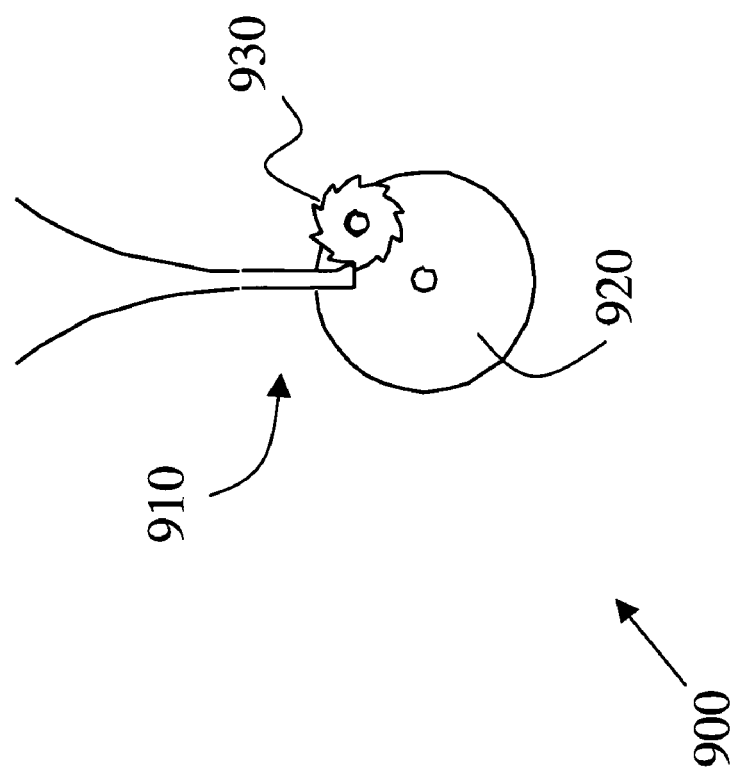
FIG. 9 shows an example of a frequency adjuster of the device according to the present invention.

FIG. 9 shows an example of an embodiment of a frequency control mechanism 900 that is accomplished by a ratchet mechanism 910 placed on frequency control knob 920. Frequency control knob 920 can extend up from an identical knob to volume control knob 610, inverted and assembled to the bottom of the element 660. A ratchet wheel 930 can be assembled to frequency control knob 920 by e.g. a snap fit, a fastener or any other means. Frequency control knob 920 can be rotated with ratchet wheel 930 in line with the main rod's travel or outside of it's travel. The ratchet wheel's rotation can be dampened by multiple methods such as e.g. a friction insert, a roll pin, a coil or a watch spring, a high friction disc, or the like. There could be a variety of ratchet wheels along the circumference of frequency control knob 920 to adjust the resistance to main rod 610 depending on the rotation direction of frequency control knob 920.

Figure 10:
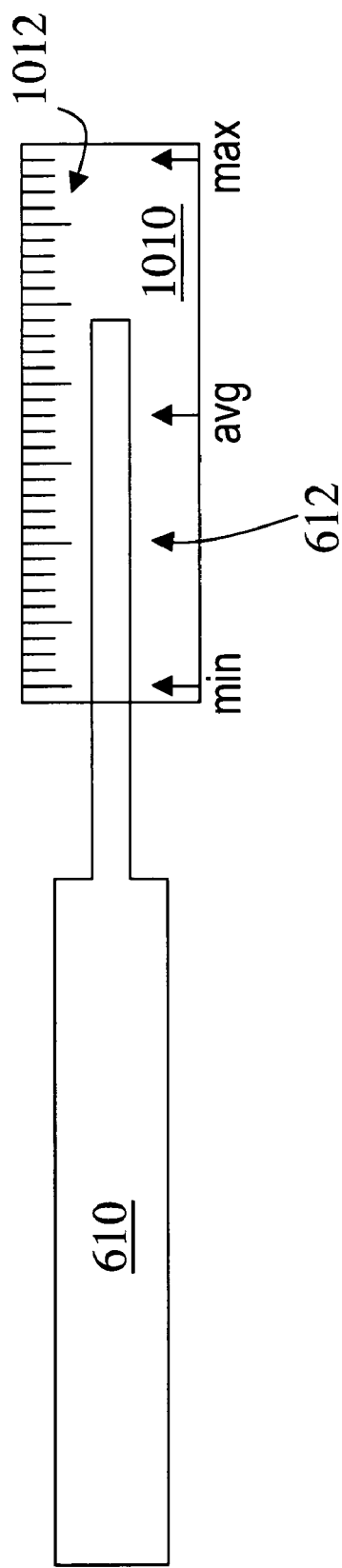
FIG. 10 shows an example of a visual feedback mechanism according to the present invention.

A visual feedback mechanism could be added to provide the user with visual feedback (colors, markings, symbols, or the like) on the adjustments to size, travel of the main shaft, or the frequency. FIG. 10 shows an example of a visual feedback mechanism for the size (volume) adjustments. Main shaft 610 could travel across a ruler 1010 designed to indicate e.g. minimum min, average avg, and maximum max deliverable tidal volume. The relative position of narrow end 612 of main shaft 610 to markings 1012 could further assist in fine-tuning the desired volume. The visual feedback mechanism could be placed inside a body whereby the body has a transparent part allowing a user to visualize the visual feedback mechanism. A similar feedback mechanism could be applied for the frequency.

One could further add an audible feedback mechanism (beeps, timers, commands, warnings, or the like) that provides feedback over the compression speed, frequency, tidal volume, setting of the size (volume) adjuster or setting of the frequency control adjuster. Another example is to have click mechanism associated with the travel of the shaft(s) and/or changes in volume. The clicking sounds could also be used as a tactile feedback; e.g. the clicks can be felt through the hand.

Figure 11:
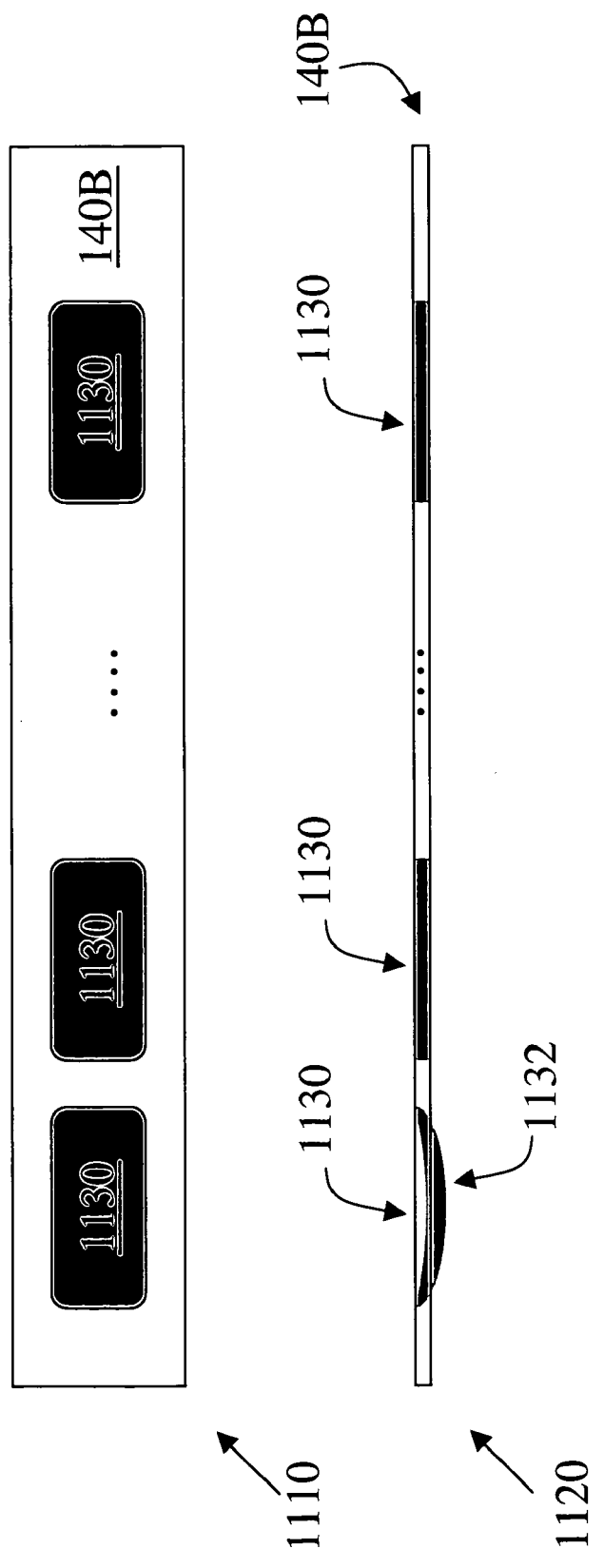
FIG. 11 shows an example of a tactile feedback mechanism according to the present invention.

In still another embodiment, one could add tactile feedback areas 1130 on one or more of panels such as panel 140B as shown in FIG. 11; 1110 is a top view and 1120 is a side view. Tactile feedback areas 1130 are sized and positioned to fit a thumb of a hand or one or more fingers (i.e. on panel 140B') of the hand. These areas are made of a flexible material that is responsive to thumb or finger pressure as well as pressure from e.g. the air/oxygen inside the body. This will provide the user additional feedback on the compression force and lung resistance. Deflection 1132 of flexible material 1130 with respect to the rigid panel 140B illustrates the deflection caused by e.g. a finger during compression.

Figure 12:
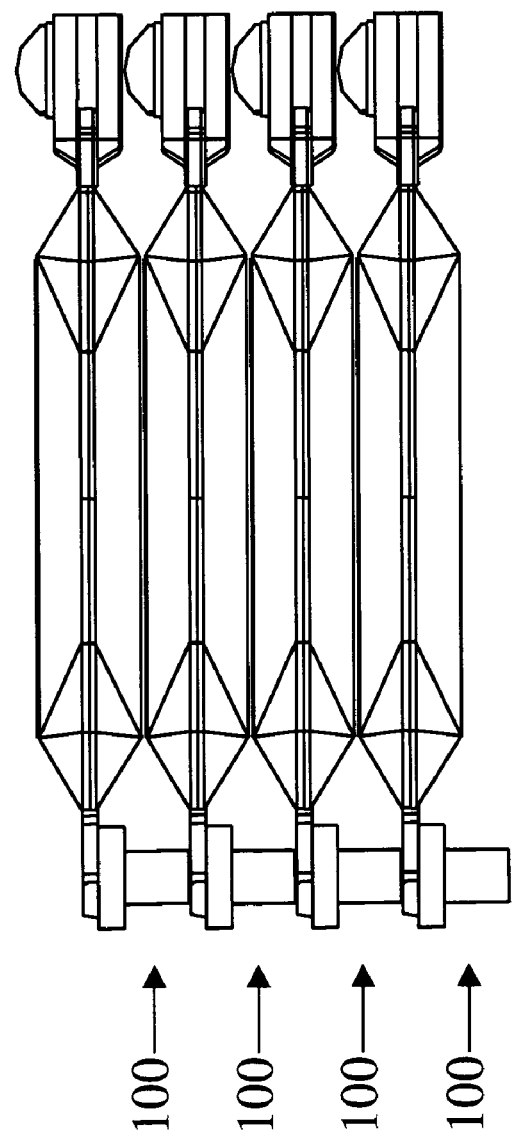
FIG. 12 shows an example of stacking or nesting the devices of the present invention.

FIG. 12 shows an example of stacking or nesting multiple devices 100 on top of each other. Stacking or nesting would be beneficial where space is limited, e.g. in an ambulance, and where multiple devices might be required. In one example the design and geometry of the inlet mechanism, body and/or output mechanism allows them to nest with one another. For example, the top of the output mechanism could nest into the bottom of another output mechanism (a similar nesting could be established for the input mechanism). Besides fitting the devices together, the device could also have features, e.g. ribs, indentations, VELCRO® (hook-and-loop fastener material), snap-mechanism, or the like, that prevent side-to-side movement.

Although the present invention and its advantages have been described in detail, it should be understood that the present invention is not limited to or defined by what is shown or discussed herein. The drawings, description and discussion herein show examples of the invention and provide examples of using the invention. One skilled in the art will realize that implementations of the present invention could be made without departing from the principles, spirit or legal scope of the present invention. Accordingly, the scope of the present invention should be determined by the following claims and their legal equivalents.

What is claimed is:

1. A ventilation or resuscitation device, comprising: a body with rigid panels encompassing a sealed volume with an inlet mechanism and an outlet mechanism, said rigid panels movable with respect to each other, wherein said body having an uncompressed state and a compressed state, wherein said body having at least a first displacement in a first direction and a second displacement in a second direction, and wherein said second displacement is a function of said first displacement and the geometry of said panels, wherein a first panel and a second panel rotate around a first axis, and wherein a third panel rotates around a second axis wherein said second axis is substantially orthogonal to said first axis.

2. The device as set forth in claim 1, further comprising a size adjuster to adjust one or more of said body displacement changes between said states.

3. The device as set forth in claim 2, wherein said size adjuster is inside said body, outside said body or intrinsic to said body.

4. The device as set forth in claim 2, wherein said size adjuster adjusts said one or more of said body displacement changes up to 170 mm.

5. The device as set forth in claim 1, further comprising a volume adjuster to adjust said volume changes between said states.

6. The device as set forth in claim 5, wherein said volume adjuster is inside said body, outside said body or intrinsic to said body.

7. The device as set forth in claim 1, further comprising a volume restoring mechanism to restore said volume from said compressed state to said uncompressed state.

8. The device as set forth in claim 7, wherein said volume restoring mechanism is inside said body, outside said body or intrinsic to said body.

9. The device as set forth in claim 1, further comprising a frequency adjuster to adjust the time to restore said volume from said compressed state to said uncompressed state or to adjust the time to compress said volume from said uncompressed state to said compressed state.

10. The device as set forth in claim 9, wherein said frequency adjuster is inside said body, outside said body or intrinsic to said body.

11. The device as set forth in claim 1, wherein any of said body displacements of each of said panels is up to 85 mm.

12. The device as set forth in claim 1, wherein the change in said volume between said states ranges from 1 to 500 cc.

13. The device as set forth in claim 1, wherein said one or more of said body displacements between said states comfortably fits between a thumb of a hand, one or more fingers of said hand and the web of said hand.

14. The device as set forth in claim 1, wherein said one or more of said body displacements between said states is defined by the natural range of a grasping motion of a hand.

15. The device as set forth in claim 1, further comprising tactile feedback areas on one or more of said rigid panels.

16. The device as set forth in claim 15, wherein said tactile feedback areas are flexible areas and sized and positioned to fit a thumb of a hand or one or more fingers of said hand.

17. The device as set forth in claim 1, further comprising a visual feedback mechanism.

18. The device as set forth in claim 1, wherein said body is transparent.

19. The device as set forth in claim 1, further comprising an audible feedback mechanism.

20. The device as set forth in claim 1, further comprising stacking or nesting capabilities for stacking said devices.

21. The device as set forth in claim 1, wherein the change in said volume between said states ranges from 250 to 1200 cc.

22. The device as set forth in claim 1, wherein the change in said volume between said states ranges from 1 to 1400 cc.

* * * * *

UNITED STATES PATENT AND TRADEMARK OFFICE
CERTIFICATE OF CORRECTION

| | | |
|---|---|---|
| PATENT NO. | : 7,537,008 B2 | Page 1 of 1 |
| APPLICATION NO. | : 11/147070 | |
| DATED | : May 26, 2009 | |
| INVENTOR(S) | : Ian L. Halpern | |

It is certified that error appears in the above-identified patent and that said Letters Patent is hereby corrected as shown below:

Column 7, line 63, please delete "rachet" and insert --ratchet--.

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,537,008 B2
APPLICATION NO. : 11/147070
DATED : May 26, 2009
INVENTOR(S) : Ian L. Halpern Page 1 of 1

It is certified that error appears in the above-identified patent and that said Letters Patent is hereby corrected as shown below:

Title page, item [73] "Assignee", delete "ArtiVent Medical Corporation" and insert --ArtiVent Corporation--.

Signed and Sealed this

Second Day of February, 2010

David J. Kappos
*Director of the United States Patent and Trademark Office*